US007560626B2

(12) United States Patent
Good et al.

(10) Patent No.: US 7,560,626 B2
(45) Date of Patent: Jul. 14, 2009

(54) PROMOTER SEQUENCE OBTAINED FROM RICE AND METHODS OF USE

(75) Inventors: Allen G. Good, Edmonton (CA); Mary DePauw, Edmonton (CA); Ashok K. Shrawat, Edmonton (CA)

(73) Assignee: Arcadia Biosciences, Inc., Davis, CA (US)

( * ) Notice: Subject to any disclaimer, the term of this patent is extended or adjusted under 35 U.S.C. 154(b) by 0 days.

(21) Appl. No.: 11/644,453

(22) Filed: Dec. 21, 2006

(65) Prior Publication Data

US 2007/0157337 A1 Jul. 5, 2007

Related U.S. Application Data

(60) Provisional application No. 60/753,848, filed on Dec. 23, 2005.

(51) Int. Cl.
| | |
|---|---|
| A01H 5/00 | (2006.01) |
| C07H 21/04 | (2006.01) |
| C12N 15/63 | (2006.01) |
| C12N 5/14 | (2006.01) |

(52) U.S. Cl. .............. 800/320.2; 536/24.1; 435/320.1; 435/419; 800/298

(58) Field of Classification Search .................. None
See application file for complete search history.

(56) References Cited

U.S. PATENT DOCUMENTS

| 5,256,558 | A | 10/1993 | Coruzzi et al. |
| 5,750,399 | A | 5/1998 | Dixon et al. |
| 5,955,651 | A | 9/1999 | Coruzzi et al. |
| 6,080,913 | A | 6/2000 | Tarczynski et al. |
| 6,084,153 | A | 7/2000 | Good et al. |
| 2004/0116682 | A1 | 6/2004 | Cheikh et al. |
| 2004/0187176 | A1 | 9/2004 | Boyes et al. |
| 2005/0015828 | A1 | 1/2005 | Good et al. |
| 2005/0044585 | A1 | 2/2005 | Good et al. |
| 2007/0020621 | A1* | 1/2007 | Boukharov et al. ............ 435/6 |
| 2007/0162995 | A1 | 7/2007 | Good et al. |

FOREIGN PATENT DOCUMENTS

| EP | 0303780 A2 | 2/1989 |
| WO | WO-90/13633 A1 | 11/1990 |
| WO | WO-91/04325 A1 | 4/1991 |
| WO | WO-93/07279 A1 | 4/1993 |
| WO | WO-95/09911 A1 | 4/1995 |
| WO | WO-97/30163 A1 | 8/1997 |
| WO | WO-01/55433 A2 | 8/2001 |
| WO | WO 01/55433 A2 * | 8/2001 |
| WO | WO-03/000898 A1 | 1/2003 |
| WO | WO 03/000898 A1 * | 1/2003 |

OTHER PUBLICATIONS

Kim et al. (Plant Mol. Biol. 24:105-117, 1994).*
Benfey et al. (Science 250:959-966, 1990).*

Back, E. et al. (1991). "Isolation of the Spinach Nitrate Reductase Gene Promoter which Confers Nitrate Inducibility on GUS Gene Expression in Transgenic Tobacco," *Plant Molecular Biology* 17:9-18.
Bohnert, H. J. et al. (Jul. 1995). "Adaptations to Environmental Stresses," *The Plant Cell* 7:1099-1111.
Cheng, C.-L. et al. (1988). "A New Locus (NIA 1) in *Arabidopsis thaliana* Encoding Nitrate Reductase," *The EMBO Journal* 7(11):3309-3314.
Cheng, C.-L. et al. (1991). "Differential Expression of the Two *Arabidopsis* Nitrate Reductase Genes," *Plant Physiology* 96:275-279.
Crawford, N. M. (Jul. 1995). "Nitrate: Nutrient and Signal for Plant Growth," *The Plant Cell* 7:859-868.
Eckes, P. et al. (1989). "Overproduction of Alfalfa Glutamine Synthetase in Transgenic Tobacco Plants," *Molecular and General Genetics* 217:263-268.
Edwards, J. W. et al. (May 1990). "Cell-Specific Expression in Transgenic Plants Reveals Nonoverlapping Roles for Chloroplast and Cytosolic Glutamine Synthetase," *Proceedings of the National Academy of Science* 87:3459-3463.
Good, A. G. et al. (1992). "Purification and Characterization of an Anaerobically Induced Alanine Aminotransferase from Barley Roots," *Plant Physiology* 99:1520-1525.
Good, A. G. et al. (Apr. 1993). "Effects of Drought Stress on the Water Relations in *Brassica* Species," *Canadian Journal of Plant Science* 73:525-529.
Good, A. G. et al. (1994). "The Effects of Drought Stress on Free Amino Acid Accumulation and Protein Synthesis in *Brassica napus*," *Physiologia Plantarum* 90:9-14.
Goodwin, T. W. et al. (1983). "Nitrogen Fixation, Amino Acid Biosynthesis and Proteins" Chapter 9 In *Introduction to Plant Biochemistry*. 2nd Edition, Pergamon Press Ltd: New York, pp. 328-361.
Guerrero, F. D. et al. (1993). "Tissue-Specific Expression of a Plant Turgor-Responsive Gene with Amino Acid Sequence Homology to Transport-Facilitating Proteins," *Plant Molecular Biology* 21:929-935.
Guerrero, F. D. et al. (1990). "Turgor-Responsive Gene Transcription and RNA Levels Increases Rapidly when Pea Shoots are Wilted. Sequence and Expression of Three Inducible Genes," *Plant Molecular Biology* 15:11-26.
Hageman, R. H. et al. (1988). "The Use of Physiological Traits for Corn Improvement" Chapter 7 In *Corn and Corn Improvement*. Sprague G. F. eds., 3rd Edition, American Society of Agronomy: Madison, WI, pp. 431-461.

(Continued)

*Primary Examiner*—Phuong T Bui
*Assistant Examiner*—Vinod Kumar
(74) *Attorney, Agent, or Firm*—Morrison & Foerster LLP

(57) ABSTRACT

Methods are provided by which *Oryza sativa* plants and seeds thereof may be modified to express a coding region of interest using a promoter sequence operatively linked to the coding region. The promoter sequence is an isolated *Oryza sativa* antiquitin (OsAnt1) promoter sequence including SEQ ID NO: 1. The coding region of interest may encode a nitrogen utilization protein, suitably alanine aminotransferase. Methods to develop *Oryza sativa* plants that have increased biomass and seed yield are also presented. Furthermore, *Oryza sativa* plants may be produced that maintain a desired yield while reducing the need for high levels of nitrogen application.

12 Claims, 8 Drawing Sheets

OTHER PUBLICATIONS

Hanson, A. D. et al. (1982). "Metabolic Responses of Mesophytes to Plant Water Deficits," *Annual Review of Plant Physiology* 33:163-203.

Hemon, P. et al. (1990). "Targeting of Glutamine Synthetase to the Mitochondria of Transgenic Tobacco," *Plant Molecular Biology* 15:895-904.

Hirel, B. et al. (1992). "Forcing Expression of a Soybean Root Glutamine Synthetase Gene in Tobacco Leaves Induces a Native Gene Encoding Cytosolic Enzyme," *Plant Molecular Biology* 20:207-218.

Jones, J. T. et al. (1995). "Developmental Expression of a Turgor-Responsive Gene that Encodes an Intrinsic Membrane Protein," *Plant Molecular Biology* 28:983-996.

Jones, M. M. et al. (1978). "Osmostic Adjustment in Leaves of Sorghum in Response to Water Deficits," *Plant Physiology* 61:122-126.

Koziel, M. G. et al. (1996). "Optimizing Expression of Transgenes with an Emphasis on Post-Transcriptional Events," *Plant Molecular Biology* 32:393-405.

Lam, H.-M. et al. (Jul. 1995). "Use of *Arabidopsis* Mutants and Genes to Study Amide Amino Acid Biosynthesis," *The Plant Cell* 7:887-898.

Montgomery, J. et al. (Jul. 1993). "Identification of an Ethylene-Responsive Region in the Promoter of a Fruit Ripening Gene," *Proceedings of the National Academy of Science* 90:5939-5943.

Morgan, J. M. (1984). "Osmoregulation and Water Stress in Higher Plants," *Annual Review of Plant Physiology* 35:299-319.

Muench, D. G. et al. (1994). "Hypoxically Inducible Barely Alanine Aminotransferase: cDNA Cloning and Expression Analysis," *Plant Molecular Biology* 24:417-427.

New England Biolabs (UK) Ltd. "Phospho-mTOR (Ser2448) Blocking Peptide #1230," located at <http://www.neb.uk.com/productcatalogue/productinfo.aspx?id=Cell%20Signaling%20Technology/1230@UK@GUEST@1@@XX@#references> visited on Jun. 26, 2007, (2 pages).

Peterman, T. K. et al. (1991). "The Glutamine Synthetase Gene Family of *Arabidopsis thaliana*: Light-Regulation and Differential Expression in Leaves, Roots and Seeds," *Molecular and General Genetics* 230:145-154.

Rhodes, D. et al. (1986). "Metabolic Changes Associated with Adaptation of Plant Cells to Water Stress," *Plant Physiology* 82:890-903.

Sakakibara, H. et al. (1995). "Isolation and Characterization of a cDNA that Encodes Maize Glutamate Dehydrogenase," *Plant and Cell Physiology* 36(5):789-797.

Skriver, K. et al. (Jun. 1990). "Gene Expression in Response to Abscisic Acid and Osmotic Stress," *The Plant Cell* 2:503-512.

Son, D. et al. (1992). "Molecular Cloning of an Alanine Aminotransferase from NAD-Malic Enzyme Type C4 Plant *Pancium miliaceum*," *Plant Molecular Biology* 20:705-713.

Son, D. et al. (Sep. 1991). "Purification and Characterization of Alanine Aminotransferase from *Panicum miliaceum* Leaves," *Archives of Biochemistry and Biophysics* 289(2):262-266.

Stewart, C. R. et al. (1977). "Inhibition of Proline Oxidation by Water Stress," *Plant Physiology* 59:930-932.

Stroeher, V. L. et al. (1995). "Molecular Cloning and Expression of a Turgor-Responsive Gene in *Brassica napus*," Plant Molecular Biology 27:541-551.

Suzuki, H. et al. (1993). "Deletion Analysis and Localization of SbPRP1, a Soybean Cell Wall Protein Gene, in Roots of Transgenic Tobacco and Cowpea," *Plant Molecular Biology* 21:109-119.

Temple, S. J. et al. (1993). "Modulation of Glutamine Synthetase Gene Expression in Tobacco by the Introduction of an Alfalfa Glutamine Synthetase Gene in Sense and Antisense Orientation: Molecular and Biochemical Analysis," *Molecular and General Genetics* 236:315-325.

Tsai, F.-Y. et al. (1990). "Dark-Induced and Organ-Specific Expression of Two Asparagine Synthetase Genes in *Pisum sativum*," *The EMBO Journal* 9(2):323-332.

Turner, N. C. (1979). "Drought Resistance and Adaptation to Water Deficits in Crop Plants" *In Stress Physiology in Crop Plants*. Mussell, H. et al. eds., John Wiley & Sons: New York, pp. 343-372.

Udvardi, M. K. et al. (1991). "Isolation and Analysis of a cDNA Clone that Encodes an Alfalfa (*Medicago sativa*) Aspartate Aminotransferase," *Molecular and General Genetics* 231:97-105.

Vanlerberghe, G. C. et al. (1991). "Communication: Anaerobic Metabolism in the N-Limited Green Alga Selenastrum minutum, III. Alanine is the Product of Anaerobic Ammonium Assimilation," *Plant Physiology* 95:655-658.

Voetberg, G. S. et al. (1991). "Growth of the Maize Primary Root at Low Water Potentials, III. Role of Increased Proline Deposition in Osmotic Adjustment," *Plant Physiology* 96:1125-1130.

Watson, J. D. et al. (1987). "Recombination at the Molecular Level" Chapter 11 *In Molecular Biology of the Gene*. Gillen, J. R. eds., Fourth Edition, The Benjamin/Cummings Publishing Company, Inc.: Menlo Park, CA, pp. 313-338.

Zehnacker, C. et al. (1992). "Purification and Properties of Tobacco Ferredoxin-Dependent Glutamate Synthase, and Isolation of Corresponding cDNA Clones," *Planta* 187:266-274.

U.S. Office Action mailed on Aug. 30, 2005, for U.S. Appl. No. 10/321,718, filed on Dec. 17, 2002, 12 pages.

U.S. Office Action mailed on May 19, 2006, for U.S. Appl. No. 10/321,718, filed on Dec. 17, 2002, 9 pages.

U.S. Office Action mailed on Jan. 17, 2007, for U.S. Appl. No. 10/321,718, filed on Dec. 17, 2002, 10 pages.

U.S. Office Action mailed on Aug. 24, 2006, for U.S. Appl. No. 10/756,213, filed on Jan. 12, 2004, 15 pages.

U.S. Office Action mailed on May 25, 2007, for U.S. Appl. No. 10/756,213, filed on Jan. 12, 2004, 9 pages.

International Search Report and Written Opinion mailed Oct. 4, 2007, for PCT Application No. PCT/US06/48857 filed Dec. 21, 2006, 8 pages.

Coruzzi, G. M. (Sep. 30, 2003). "Primary N-Assimilation Into Amino Acids in *Arabidopsis*," *The Arabidopsis Book*, pp. 1-17.

Good, A. G. et al. (1989). "Anaerobic Induction of Alanine Aminotransferase in Barley Root Tissue," *Plant Physiology* 90:1305-1309.

International Search Report and Written Opinion mailed Mar. 20, 2008, for PCT Application No. PCT/US06/49241 filed Dec. 21, 2006, 15 pages.

Iturriaga, G. et al. (1992). "Expression of Desiccation-Related Proteins from the Resurrection Plant Craterostigma plantagineum in Transgenic Tobacco," *Plant Molecular Biology* 20:555-558.

Kaye, C. et al. (1998). "Characterization of a Gene for Spinach CAP160 and Expression of Two Spinach Cold-Acclimation Proteins in Tobacco," *Plant Physiology* 116:1367-1377.

Kikuchi, H. et al. (1999). "Molecular Characterization of a Gene for Alanine Aminotransferase from Rice (*Oryza sativa*)," *Plant Molecular Biology* 39:149-159.

Kim. J. et al. (Jan. 2002). "Constitutive Overexpression of Cystathionine Gamma-Synthase in *Arabidopsis* Leads to Accumulation of Soluble Methionine and S-Methylmethionine," *Plant Physiology* 128:95-107.

Liaw, S.-H. et al. (Jun. 1993), "Feedback Inhibition of Fully Unadenylylated Glutamine Synthetase from *Salmonella typhimurium* by Glycine, Alanine, and Serine," *Proceedings of the National Academy of Sciences of the United States of America* 90:4996-5000.

Muench, D. G. et al. (1998). "Cloning and Expression of a Hypoxic and Nitrogen Inducible Maize Alanine Aminotransferase Gene," *Physiologia Plantarum* 103:503-512.

O'Neal, T. D. et al. (1975). "Pea Leaf Glutamine Synthetase," *Plant Physiology* 55:968-974.

Spencer, T. M. et al. (1992). "Segregation of Transgenes in Maize," *Plant Molecular Biology* 18:201-210.

Tzchori, I. B.-T. et al. (Nov. 1996). "Lysine and Threonine Metabolism are Subject to Complex Patterns of Regulation in *Arabidopsis*," *Plant Molecular Biology* 32(4):727-734.

U.S. Office Action mailed on Feb. 5, 2008, for U.S. Appl. No. 10/321,718, filed on Dec. 17, 2002, 9 pages.

Wakasa, K. et al. (2006), "High-Level Tryptophan Accumulation in Seeds of Transgenic Rice and its Limited Effects on Agronomic Traits and Seed Metabolite Profile," *Journal of Experimental Botany*, pp. 1-10.

Benfey, P. N. et al. (1990). "Tissue-Specific Expression from CaMV 35S Enhancer Subdomains in Early Stages of Plant Development," *The EMBO Journal* 9(6):1677-1684.

\* cited by examiner

FIGURE 1: Schematic of Key Steps in Nitrogen Utilization in a Plant Cell
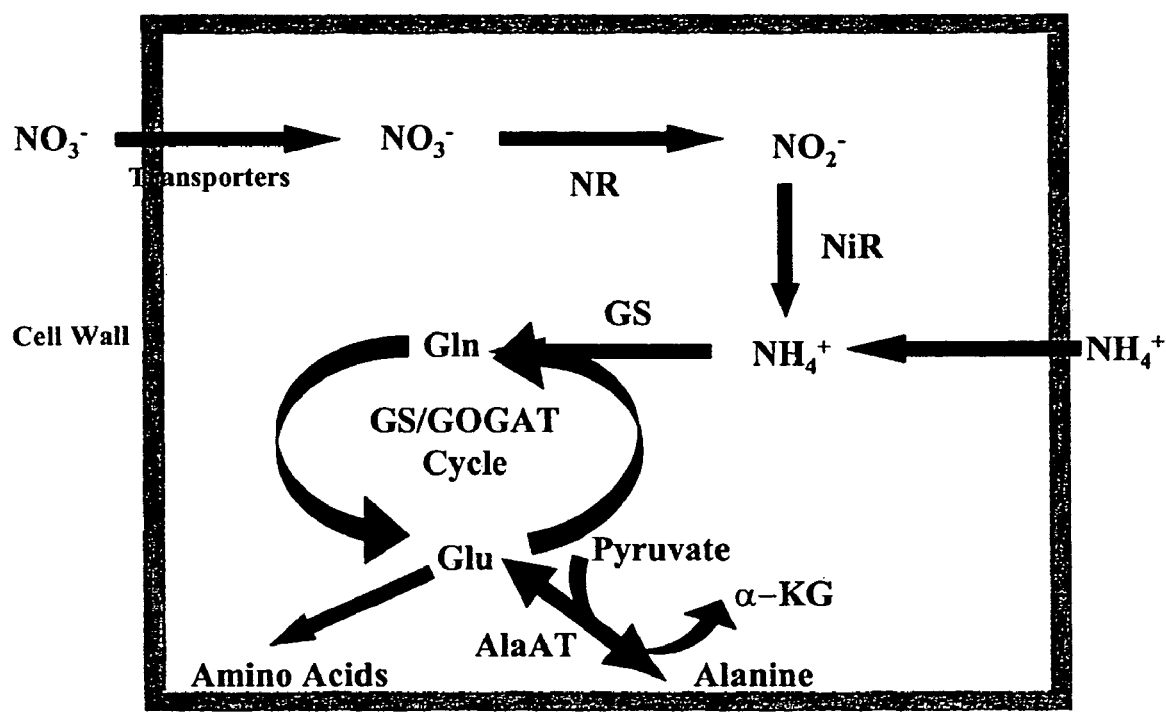

FIGURE 2

OsAnt1 regulatory region

```
    Primer 1
  1 AGGAAGTGAT TTTTAGCGTA GCTGTGTTTG TAGCGTAATT GCGTAAAGTC CTTTCAATTT
 61 TGCTATATCT CACTCGAAAG ATTTTTTCTT ATCTCTCACT CGATTTTCTC ACTCAAATTT
121 ACAGTGTATT TTCTTGTAAG TTACAGTGTA ATTTATGAAA CTTACACTGT AACTTTTGTA
181 AGTTACACTG TAATTTTTGA ATCTTCACAT GTAAATTTTA AATTTTGTAT TGGATTTGGT
241 CTTTTTCTTG AGGATATGGT AATTTAATGT TCATTATGGT GTTTCTTAAT TGCTTTTTGC
301 TTTTTATTAT ATCTATCGGA TTTTAATACA AAGATTAAAA ATCTGTGTGA TACGATTATA
361 AAAATCTTTC GAAAGATGTA TAGGTACTCC CAAGCCCTTT TAAGAAAGTT TTTCAAGACA
421 AAAGTTTTTG GATGAAAGGT AGTTATAGGG AAAAAGGAAT GTGCGTTTAT GTTTATTTGC
481 ATTGCTTATT GGCAACCAAA AACTAATCTA TAAGTAAATC TTTTATATAC GTGCGCTTAA
541 TAATTCAAAA GCAAATTCAT GTAAAATAAA ATGCGATGAA GAAACTTTAA AAAGTTATCA
601 AATTTAGATT TTATTAAATT TTAGTTTACA AGAGCGCTAC GATGAAGGCT TTAAAAAGAT
661 GGGAAAATAA AACCTTTGAC CTTTCTGGAC TTCACCAAAC AGCTCACGCT TTCGGCTTCG
721 TGCCGTCTCG TCCCGTGCTA CTGCTACCCC CTCCTGACCC CACCCGCCAC TCCACGCTCC
781 CTTCTCCTCC CCTTCCCGTG ACACACAGTC CCCACTCCAC CGCCTCCGTA TAAGTATCCC
841 TTCCTTACCG CCGGCCAGCC ACAGCCACCG CCTCCCCCAC CCCACCCCGA TCCCCTCCCC
901 GCCGTACGGG CGCAGAAGGA ACCCGTCTTC TAGAAGGAGG AGGAGGGCTA CCTCTCTCTC
961 TCTCTCTTCT GCC
    Primer 2
```

FIGURE 3: Schematic Representation of the Steps for Producing the OsAnt1pro-Gus Construct
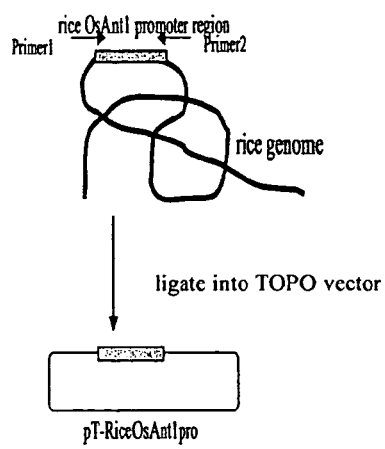
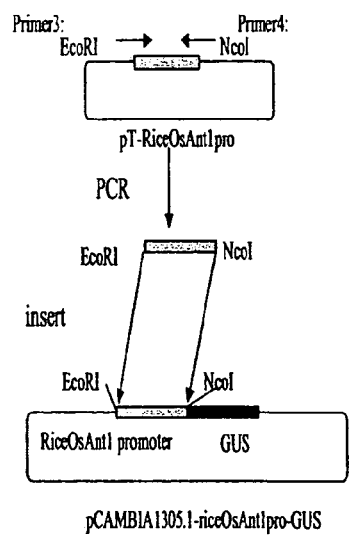

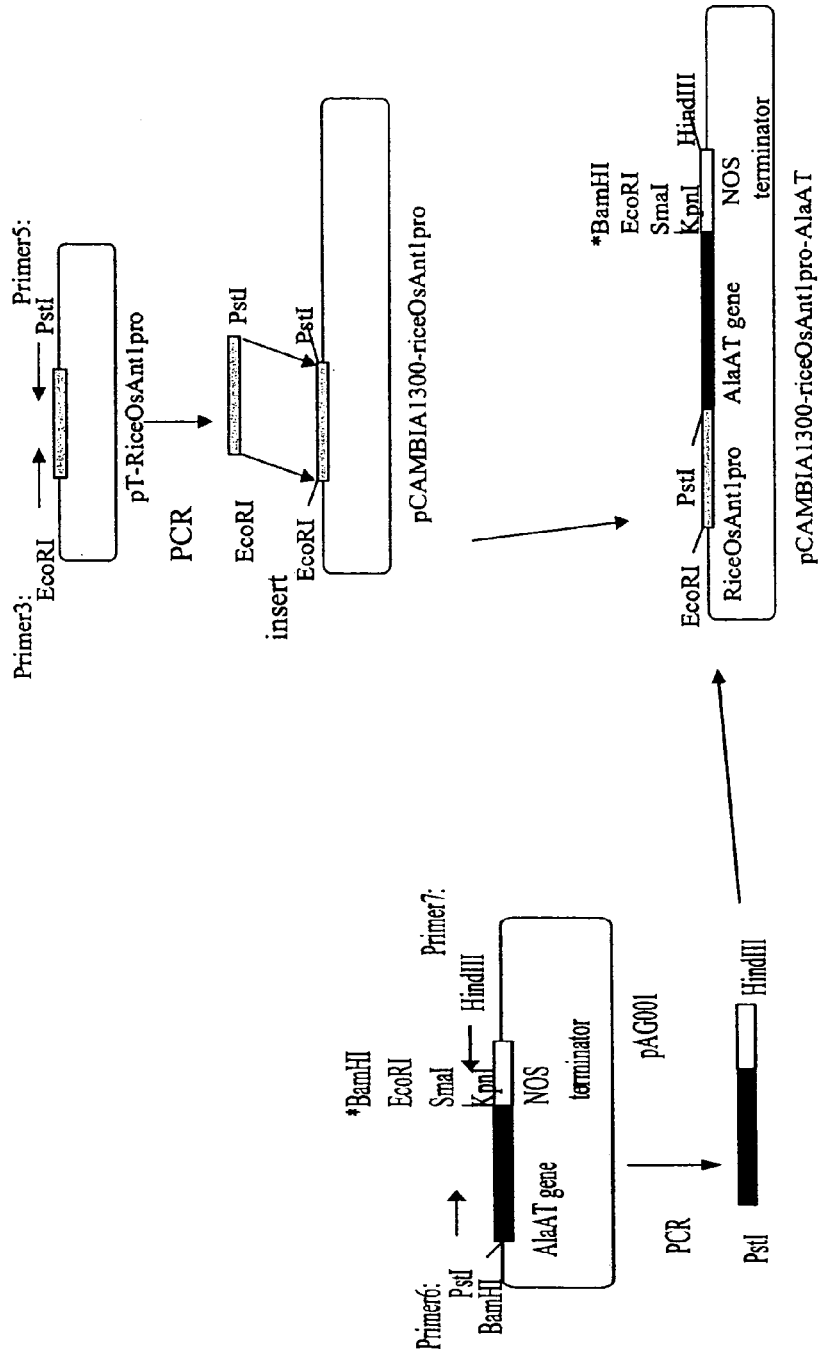
FIGURE 4: Schematic Representation of the Steps for Producing the OsAnt1pro-AlaAT Construct

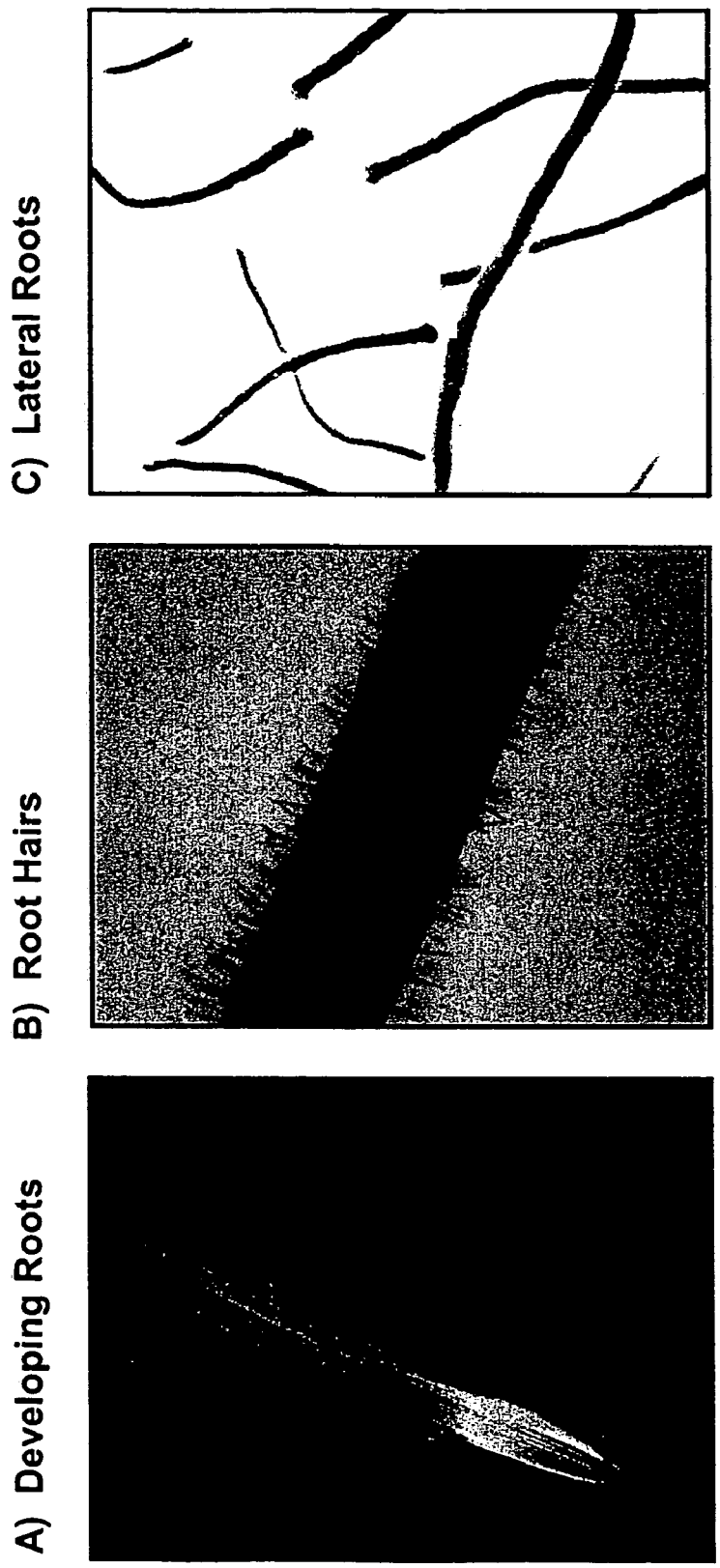
FIGURE 5: Expression of the GUS Reporter Gene Directed by the OsAnt1 Promoter
A) Developing Roots
B) Root Hairs
C) Lateral Roots

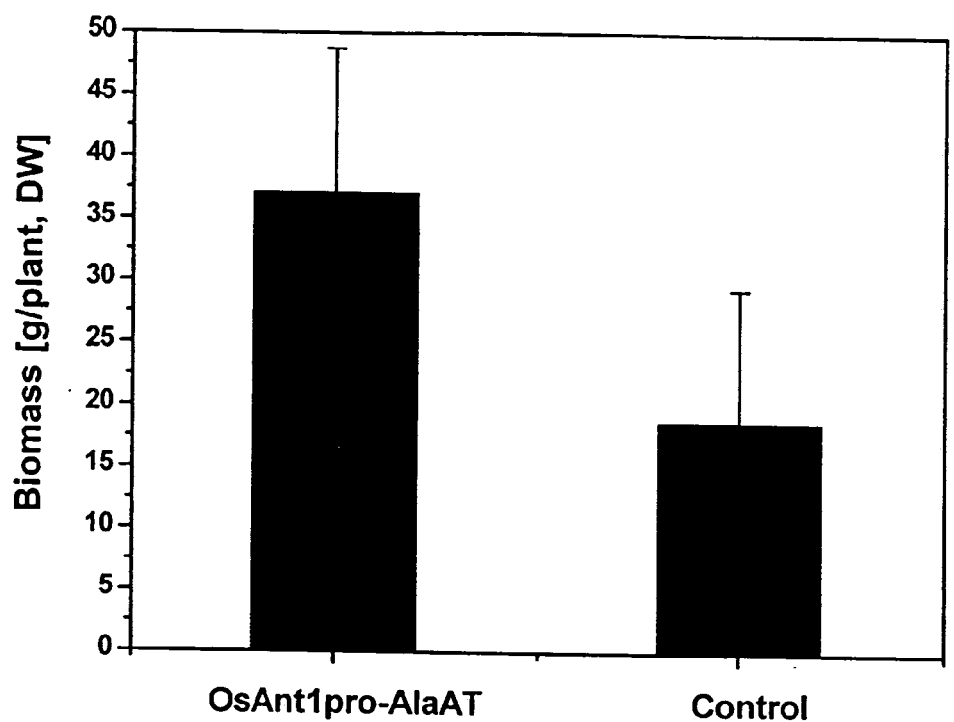
FIGURE 6: Average Dry Weight Biomass of *Oryza sativa* Plants Transformed with OsAnt1pro-AlaAT FIGURE 7: Average Total Seed Weight of *Oryza sativa* Plants Transformed with OsAnt1pro-AlaAT
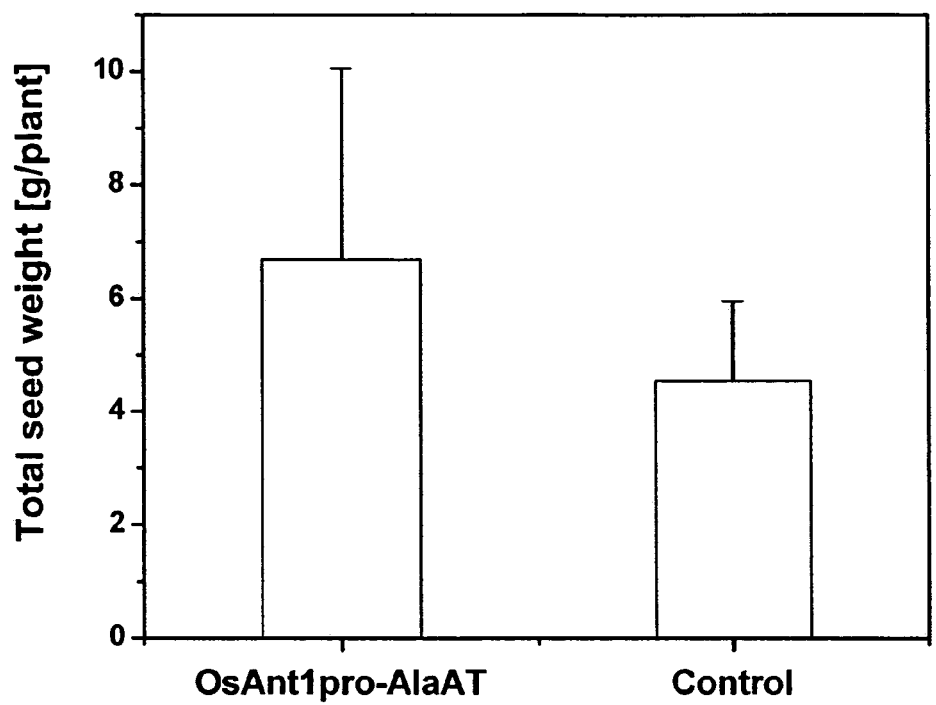

FIGURE 8: The Relationship between Dry Weight Biomass and Total Seed Weight of *Oryza sativa* Plants Transformed with OsAnt1pro-AlaAT
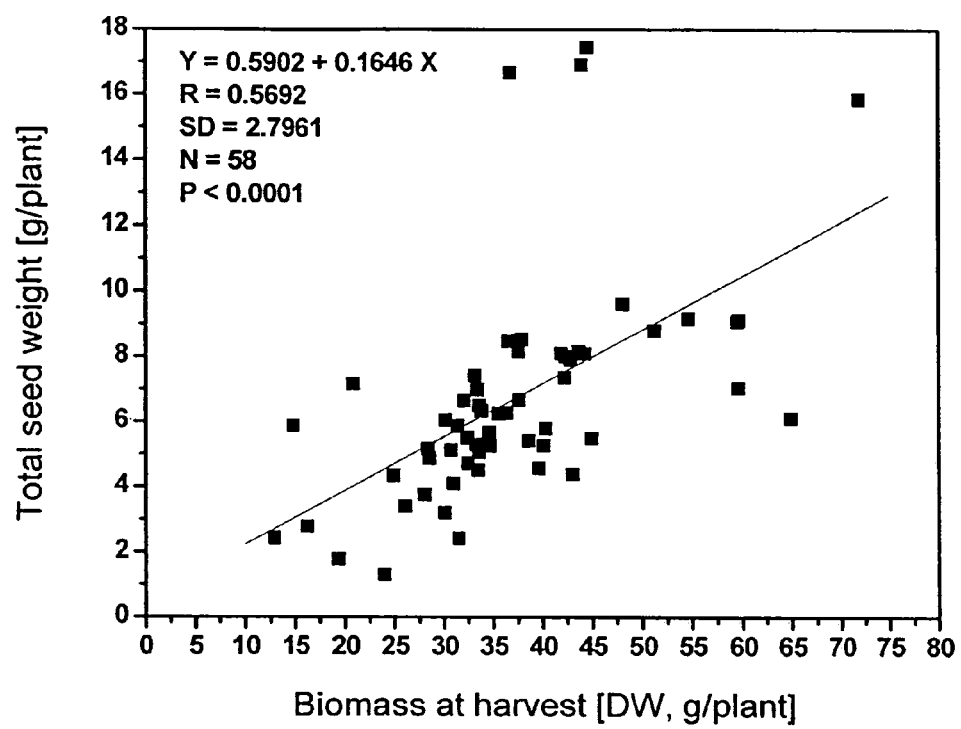

SEQUENCE LISTING

```
<160> NUMBER OF SEQ ID NOS: 8

<210> SEQ ID NO 1
<211> LENGTH: 973
<212> TYPE: DNA
<213> ORGANISM: Oryza sativa

<400> SEQUENCE: 1
aggaagtgat ttttagcgta gctgtgtttg tagcgtaatt gcgtaaagtc ctttcaattt      60
tgctatatct cactcgaaag attttttctt atctctcact cgattttctc actcaaattt     120
acagtgtatt ttcttgtaag ttacagtgta atttatgaaa cttacactgt aactttttgta    180 agttacactg taattttga atcttcacat gtaaatttta aattttgtat tggatttggt     240 cttttttcttg aggatatggt aatttaatgt tcattatggt gtttcttaat tgcttttttgc    300 ttttattat atctatcgga ttttaataca aagattaaaa atctgtgtga tacgattata      360
aaaatctttc gaaagatgta taggtactcc caagcccttt taagaaagtt tttcaagaca     420
aaagtttttg gatgaaaggt agttataggg aaaaaggaat gtgcgtttat gtttatttgc     480
attgcttatt ggcaaccaaa aactaatcta taagtaaatc ttttatatac gtgcgcttaa     540
taattcaaaa gcaaattcat gtaaaataaa atgcgatgaa gaaactttaa aaagttatca     600
aatttagatt ttattaaatt ttagtttaca agagcgctac gatgaaggct ttaaaaagat     660
gggaaaataa aacctttgac ctttctggac ttcaccaaac agctcacgct ttcggcttcg    720
tgccgtctcg tcccgtgcta ctgctacccc ctcctgaccc cacccgccac tccacgctcc    780
cttctcctcc ccttcccgtg acacacagtc cccactccac cgcctccgta taagtatccc     840
ttccttaccg ccggccagcc acagccaccg cctcccccac cccacccga tcccctcccc     900 gccgtacggg cgcagaagga acccgtcttc tagaaggagg aggagggcta cctctctctc     960
tctctcttct gcc                                                       973

<210> SEQ ID NO 2
<211> LENGTH: 24
<212> TYPE: DNA
<213> ORGANISM: Artificial Sequence
<220> FEATURE:
```

-continued

```
<223> OTHER INFORMATION: Synthetic Construct

<400> SEQUENCE: 2
aggaagtgat ttttagcgta gctg                                          24

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
atggcagaag agagagagag agagg                                         25

<210> SEQ ID NO 4
<211> LENGTH: 21
<212> TYPE: DNA
<213> ORGANISM: Artificial Sequence
<220> FEATURE:
<223> OTHER INFORMATION: Synthetic Construct

<400> SEQUENCE: 4
ggaattcagg aagtgatttt t                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic Construct

<400> SEQUENCE: 5
catgccatgg atggcagaag a                                             21

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
aactgcagat ggcagaaga                                                19

<210> SEQ ID NO 7
<211> LENGTH: 21
<212> TYPE: DNA
<213> ORGANISM: Artificial Sequence
<220> FEATURE:
<223> OTHER INFORMATION: Synthetic Construct

<400> SEQUENCE: 7
aactgcagat ggctgccacc g                                             21

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
cccaagcttc ccgatctagt a                                             21
```

PROMOTER SEQUENCE OBTAINED FROM RICE AND METHODS OF USE

CROSS-REFERENCE TO RELATED APPLICATIONS

This application claims the benefit of U.S. Provisional App. No. 60/753,848, filed Dec. 23, 2005, which is herein incorporated by reference in its entirety.

FIELD OF INVENTION

The present invention relates to a promoter sequence obtained from rice, to methods of using the promoter sequence, and to plants including the promoter sequence.

BACKGROUND OF THE INVENTION

Crop plants have a fundamental dependence on inorganic nitrogenous fertilizers, principally in the form of nitrate ($NO_3^-$) and ammonium ($NH_4^+$). Each year, approximately 85 to 90 million metric tons (MMt) of nitrogenous fertilizers are added to the soil worldwide. This amount is up from only 1.3 MMt in 1930 and from 10.2 MMt in 1960. It is predicted to increase to 240 MMt by the year 2050 (Tilman et al., 1999, *Proc. Nat. Acad. Sci. USA.* 96: 5995-6000). It is estimated that 50% to 70% of the applied nitrogen is lost from the plant-soil system. Because $NO_3^-$ is soluble and not retained by the soil matrix, excess $NO_3^-$ may leach into the water and may be depleted by microorganisms.

It is important to improve the nitrogen use efficiency (NUE) of crop plants for two reasons. First, the use of commercial fertilizers accounts for one of the major costs associated with the production of high yielding crops. Second, it would be an environmental benefit to reduce the levels of nitrogenous fertilizers that are lost into the ecosystem. Environmental effects include the deterioration of soil quality, pollution and health hazards.

Alanine is one of the more common amino acids in plants. Alanine is synthesized by the enzyme alanine aminotransferase (AlaAT) from pyruvate and glutamate in a reversible reaction as shown in FIG. 1. Alanine is an amino acid that is known to increase under other specific environmental conditions such as drought and anaerobic stress (Muench and Good, 1994, *Plant Mol. Biol.* 24:417-427; Vanlerberge et al., 1993, *Plant Physiol.* 95:655-658). Alanine levels are known to increase substantially in root tissue under anaerobic stress. As an example, alanine levels in barley roots increase 20-fold after 24 hours of anaerobic stress. The AlaAT gene is induced by light in broom millet and when plants are recovering from nitrogen stress (Son et al., 1992, *Arch. Biochem. Biophys.* 289: 262-266). Vanlerberge et al. (1993) have shown that in nitrogen-starved anaerobic algae, the addition of nitrogen in the form of ammonia resulted in 93% of an $N_{15}$ label being incorporated directly into alanine. Thus, alanine appears to be an important amino acid in stress response in plants.

U.S. Pat. No. 6,084,153 discloses the induction of AlaAT in the roots of canola plants and a resulting nitrogen efficient phenotype.

WO 01/55433 teaches the use of *Brassica* turgor gene-26 (btg26). The turgor gene-26-like proteins have recently been named antiquitins (Tang et al., 2002, *FEBS Lett.* 516 (1-3): 183-186). *Brassica napus* plants were transformed with constructs containing the AlaAT gene in operative linkage with the btg26 promoter. The transgenic plants were shown to have elevated levels of AlaAT in the root tissue.

US2005/0044585 discloses the use of promoters LeAMT1, LeNRT1, GmNRT2, KDC1, PHT1, GOGAT, OsRAB5 and ALF5 to direct root specific expression of a gene encoding a nitrogen utilization protein, for example, AlaAT.

Increasing NUE within rice is also desired within the art. In 2006, worldwide acreage devoted to growing rice was 151,730,000 hectares with nitrogen consumption estimated at 11,963 MMT. Thus, improving NUE in rice would not only decrease the cost of crop production but would reduce the harmful environmental effects of nitrogen fertilizers including the development of "dead zones" in the world's oceans that result from the death and decomposition of massive algae blooms fed by excessive nutrient runoff.

SUMMARY OF THE INVENTION

Objectives of the present invention are to provide a promoter sequence obtained from *Oryza sativa* (rice), methods for using the promoter sequence, and plants including the promoter sequence.

In one embodiment, the present invention provides methods by which *Oryza sativa* may be modified to express a target gene or coding region of interest using a promoter sequence operatively linked to the coding region. In another embodiment, the present invention also provides methods of producing *Oryza sativa* plants that have increased biomass and seed yield. By increasing the biomass and seed yield, *Oryza sativa* plants are provided that have an environmental benefit in that they can maintain a desired yield while reducing the need for high levels of nitrogen application.

An isolated *Oryza sativa* antiquitin (OsAnt1) promoter sequence including SEQ ID NO: 1 and active fragments thereof are disclosed.

Also provided is a genetic construct including an OsAnt1 promoter sequence including SEQ ID NO: and active fragments thereof operatively linked with a coding region of interest encoding a target protein. The target protein may be a nitrogen utilization protein, for example, alanine aminotransferase (AlaAT).

A vector including a genetic construct with an OsAnt1 promoter sequence including SEQ ID NO: 1 and active fragments thereof operatively linked with a coding region of interest encoding a target protein. The target protein may be a nitrogen utilization protein, for example, AlaAT.

A method for directing expression of a target gene in an *Oryza sativa* plant is described. The method may include contacting and introducing into an *Oryza sativa* plant the target gene in operative linkage with an OsAnt1 promoter sequence including SEQ ID NO: 1 and active fragments thereof and expressing the target gene. The target gene may encode a nitrogen utilization protein, for example, AlaAT. Furthermore, expression of the target gene may be targeted to a particular tissue, for example, to the root of the plant.

Also described is a method for increasing biomass of an *Oryza sativa* plant by contacting and introducing into an *Oryza sativa* plant a target gene in operative linkage with an OsAnt1 promoter sequence including SEQ ID NO: 1 and active fragments thereof. The target gene may encode a nitrogen utilization protein, for example, AlaAT. Furthermore, expression of the target gene may be targeted to a particular tissue, for example, to the root of the plant.

A method for increasing seed yield of an *Oryza sativa* plant is also described. The method my include contacting and introducing into an *Oryza sativa* plant a target gene in operative linkage with an OsAnt1 promoter sequence including SEQ ID NO: 1 and active fragments thereof. The target gene may encode a nitrogen utilization protein, for example, AlaAT. Furthermore, expression of the target gene may be targeted to a particular tissue, for example, to the root of the plant.

Also described is a transformed *Oryza sativa* plant including a target gene in operative linkage with an OsAnt1 promoter sequence including SEQ ID NO: 1 and active fragments thereof. The target gene may encode a nitrogen utilization protein, for example, AlaAT.

*Oryza sativa* plant seed including a target gene in operative linkage with an OsAnt1 promoter sequence including SEQ ID NO: 1 and active fragments thereof are described. The target gene may encode a nitrogen utilization protein, for example, AlaAT.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a schematic representation of the key steps in nitrogen utilization in a plant cell. Nitrate ($NO_3^-$) is transported into the plant cell and converted to nitrite ($NO_2^-$) by nitrate reductase (NR). Nitrite is translocated from the cytoplasm to the chloroplast where it is reduced by nitrite reductase (NiR) to ammonium ($NH_4^+$). Glutamine synthetase (GS) functions in assimilating or recycling ammonium. An enzyme couple, glutamine synthetase (GS)/glutamate synthase (GOGAT), catalyzes the conversion of glutamine (Gln) to glutamate (Glu). Glutamate is a building block of many amino acids. In addition, alanine is synthesized by the enzyme alanine aminotransferase (AlaAT) from pyruvate and glutamate in a reversible reaction.

FIG. 2 shows the nucleotide sequence for the OSAnt1 promoter of the present invention (SEQ ID NO:1). The sequence was isolated using a blastn search of the NCBI database using the nucleotide sequence (366-3175 bp) of the *Brassica* btg26 gene (Stroeher et al., 1995, *Plant Mol. Biol.* 27:541-551) to identify the homologous rice nucleotide sequence (accession number AF323586). This sequence was then used in turn against the TIGR *Oryza sativa* sequencing project (see: tigr.org/tdb/e2k1/osa1/), as set out in Example 1. The putative TATA box is shown in bold and the primers used in PCR amplifying the sequence from the rice genome are underlined.

FIG. 3 shows a schematic representation of the steps for producing the genetic construct OsAnt1pro-Gus, using the reporter gene beta-glucuronidase (GUS) in accordance with the method described in Example 2.

FIG. 4 shows a schematic representation of the steps for producing the genetic construct OsAnt1pro-AlaAT in accordance with the method described in Example 2.

FIG. 5 shows expression of the GUS reporter gene directed by the OsAnt1 promoter of the present invention. Expression is present in the cell expansion area of root tips of developing roots (panel A); in root hairs of developing roots (panel B); and in lateral roots of roots (panel C) of an *Oryza sativa* plant transformed with the genetic construct OsAnt1pro-Gus as shown in FIG. 3, in accordance with the method described in Example 3. Darkly stained areas indicate expression of the GUS reporter gene.

FIG. 6 shows the average dry weight biomass (grams) of *Oryza sativa* plants transformed with the genetic construct OsAnt1pro-AlaAT as shown in FIG. 4 compared to the average dry weight biomass (grams) of control, wild-type *Oryza sativa* plants grown under the same growth conditions as given in Example 3.

FIG. 7 shows the average total seed weight (grams) of seeds collected from *Oryza sativa* plants transformed with the genetic construct OsAnt1pro-AlaAT as shown in FIG. 4 compared to the average total seed weight (grams) of seeds collected from control, wild-type *Oryza sativa* plants grown under the same growth conditions as given in Example 3.

FIG. 8 shows the relationship between dry weight biomass (grams) and total seed weight (grams) for each transgenic plant.

DETAILED DESCRIPTION

A promoter sequence obtained from rice, methods of using the promoter sequence, and a rice plant and a portion of a rice plant including the promoter sequence as described.

The following description is of a preferred embodiment.

A promoter sequence for directing expression of a coding region of interest within an *Oryza sativa* plant is described. The promoter sequence is an isolated *Oryza sativa* antiquitin (OsAnt1) promoter sequence including SEQ ID NO: 1 and active fragments thereof.

The language "coding region of interest" includes any gene that is desirably expressed in one or more than one plant tissue. Examples of a coding region of interest which may advantageously be utilized in conjunction with the methods described herein include nucleic acid sequences that encode one or more than one protein involved in nitrogen assimilation, nitrogen utilization, or a combination thereof. Other examples would be nucleic acid sequences encoding one or more than one protein involved in nitrogen uptake and utilization.

By "promoter" it is meant the sequence of a DNA molecule that directs transcription of a downstream gene to which it is operatively linked or that, when fused to a particular gene and introduced into a cell, causes expression of the gene at a level higher than is possible in the absence of the DNA sequence. Such promoters can be the full length promoter or active fragments thereof. By "active fragment" is meant a fragment that has at least about 0.1%, preferably at least about 10%, and more preferably at least about 25% of the activity of a reference promoter sequence as tested via methods known to those of skill in the art for detecting promoter activity, e.g., measurement of GUS reporter gene levels. DNA sequences necessary for activity can be identified by synthesizing various fragments and testing for expression or introducing point mutations in certain regions and testing for loss of activity.

Heterologous fragments of promoters or other promoter sequences may be combined to mediate the activity of a promoter sequence. For example, the CaMV 35S promoter or other known promoter sequences may be combined with the promoter sequence described herein to mediate expression of a coding region of interest.

The gene constructs described herein can also include further enhancers, either translation or transcription enhancers, as may be required. These enhancer regions are well known to persons skilled in the art and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region or from the structural gene. The sequence can also be derived from the promoter selected to express the gene and can be specifically modified to increase translation of the mRNA.

The gene constructs described herein can further include a 3' untranslated (or terminator) region that contains a polyadenylation signal and other regulatory signals capable of effecting mRNA processing or gene expression. Nonlimiting examples of suitable 3' regions are the 3' transcribed non-translated regions containing a polyadenylation signal of *Agrobacterium* tumour-inducing (Ti) plasmid genes such as the nopaline synthase (Nos gene), plant genes such as the soybean storage protein genes, and the small subunit of the ribulose-1,5-bisphosphate carboxylase (ssRUBISCO) gene.

By "operatively linked" or "operative linkage" it is meant that the particular sequences interact either directly or indirectly to carry out an intended function, such as mediation or modulation of gene expression. The interaction of operatively linked sequences may be mediated, for example, by proteins that interact with the operatively linked sequences.

The term "exogenous" as used herein in reference to a nucleic acid molecule means a nucleic acid molecule originating from outside the plant. An exogenous nucleic acid molecule can have a naturally occurring or non-naturally occurring nucleotide sequence. One skilled in the art understands that an exogenous nucleic acid molecule can be a heterologous nucleic acid molecule derived from the same plant species or a different plant species than the plant into which the nucleic acid molecule is introduced. Alternatively, it can be a nucleic acid molecule derived from a non-plant species such as fungi, yeast, bacteria or other non-plant organisms.

Because the level of transgene expression in monocots is generally higher when driven by a monocot promoter rather than a dicot promoter, the rice genome was examined to identify a rice homologue of btg26. This was done using a blastn search using the amino acid sequence of the *Brassica* btg26 gene (Stroeher et al., 1995, *Plant Mol. Biol.* 27:541-551) against the TIGR *Oryza sativa* sequencing project (see Example 1). The *Oryza sativa* antiquitin (OsAnt1) gene was identified on chromosome 9 of rice and a promoter sequence, upstream (5') to the ATG start codon of OsAnt1 gene was identified (FIG. 2; SEQ ID NO: 1). This promoter sequence was used to drive the expression of a coding region of interest. Plants expressing, for example but not limited to, AlaAT under control of the OsAnt1 promoter sequence exhibited increased biomass, seed yield and NUE (See Example 3).

Therefore, the production of *Oryza sativa* plants that express one or more target genes or coding regions of interest are described. Further provided is a method for increasing biomass of a rice plant and a method for increasing seed yield of a rice plant. By the methods described herein, it is possible to produce rice plants having one or more desired traits or properties; e.g., to alter specifically the genetic properties of the plant, the physiological properties of the plant, or both the genetic and the physiological properties of the plant. In addition, methods of producing rice plants having expression in the roots of one or more than one desired gene or coding region of interest, using the OsAnt1 promoter sequence disclosed herein are described.

The production of rice plants having expression of one or more than one target gene or coding region of interest is accomplished using the OsAnt1 promoter sequence of the present invention, which directs expression of the coding region of interest. The OsAnt1 promoter sequence enables expression of the target sequence in one or more than one tissue of the rice plant, suitably in the root tissue.

It will be understood by one skilled in the art that modifications may be made to the OsAnt1 promoter sequence useful in the methods and constructs of the invention to improve or modulate the activity of the promoter sequence. Selected regions of the OsAnt1 promoter sequence may be operatively linked to a single target coding region to alter the expression level of the linked coding region, or the OsAnt1 promoter sequence may be operatively linked to one or more than one target coding regions such that the expression of each target coding region may be coordinately regulated. The OsAnt1 promoter sequence may be of any size appropriate to permit its functioning as a promoter. The OsAnt1 promoter sequence may be modified using standard methods known within the art, for example but not limited to, mutagenesis, deletion, insertion, substitution, or truncation, to alter the degree to which the operatively linked coding region is expressed, or to alter the specificity of expression directed by the promoter sequence. Further, the placement of the OsAnt1 promoter sequence relative to the operatively linked coding region may be modulated (e.g., moved further away or closer together) to attain a desired level of promoter-directed expression.

It is envisaged that the OsAnt1 promoter sequence may direct expression of the coding region of interest in response to a specific environmental or physiological condition. For example, the promoter sequence may be activated under conditions of drought stress, osmotic stress, salt stress, temperature stress, nutrient deprivation, or under specific developmental conditions for example but not limited to, upon germination, fruiting, or seed production.

A coding region of interest, or a target gene, of the invention may be any nucleotide sequence that is desirably expressed within a rice plant. General classes of coding regions which may be advantageously employed in the methods and constructs of the invention include nucleotide sequences encoding structural proteins; proteins involved in the transport of nitrogen; proteins involved in the uptake of nitrogen; proteins involved in both the transport and uptake of nitrogen; enzymes and proteins involved in nitrogen utilization; proteins involved in plant resistance to pesticides or herbicides; proteins involved in plant resistance to nematodes, viruses, insects, or bacteria; proteins involved in plant resistance to stress, for example but not limited to osmotic, temperature, pH, or oxygen stress; proteins involved in stimulation or continuation of plant growth; proteins involved in phytoremediation; or proteins having pharmaceutical properties or encoding enzymes which produce compounds having pharmaceutical properties.

For example, the coding region of interest may encode a nitrogen utilization protein and, in particular, an enzyme that assimilates ammonia into amino acids or uses the formed amino acids in biosynthetic reactions. This protein may be selected from, but not limited to, a nitrate transporter (high or low affinity), an ammonium transporter, an ammonia transporter, an amino acid transporter, alanine dehydrogenase, glutamine synthetase (GS), asparagine synthetase (AS), glutamate synthase (also known as glutamate 2:oxogluturate amino transferase and GOGAT), asparaginase (ANS), glutamate dehydrogenase (GDH), nitrate reductase, aspartate aminotransferase (AspAT), alanine aminotransferase (AlaAT), and other known aminotransferases. Such proteins are disclosed in US Patent Application Publication Number 2005/0044585, which is hereby incorporated by reference in its entirety.

The target gene or coding region of interest may be naturally expressed in the rice plant or it may be heterologous to the rice plant. The gene may originate from any source, including viral, bacterial, plant or animal sources. Preferably, the coding region of interest is heterologous to the OsAnt1 promoter sequence to which it is operatively linked, in that it is not from the gene the OsAnt1 promoter sequence is naturally linked to.

The coding region can be modified in any suitable way in order to engineer a gene or rice plant with desirable properties. The coding region can be modified to be transcribable and translatable in the plant system; for example, the nucleotide sequence encoding the protein of interest can be modified such that it contains all of the necessary poly-adenylation sequences, start sites and termination sites which allow the coding sequence to be transcribed to mRNA (messenger ribonucleic acid) and the mRNA to be translated in the rice plant. Further, the coding region may be modified such that its codon usage is more similar to that of native genes of the rice plant (i.e., plant optimized sequence may be used). Such nucleotide sequence modifications and the methods by which they may be made are well known to one of skill in the art.

The constructs described herein include an OsAnt1 promoter sequence-coding region of interest are most efficiently introduced into a rice plant, a rice plant cell or plant protoplast through the use of a vector. Examples of cloning or expression vectors suitable for use with the invention are plasmids (such as pAG001), cosmids, viral DNA or RNA, and minichromosomes. Appropriate plant vectors are well known in the art (see, e.g., Clark, M., ed. (1997) *Plant Molecular Biology. A Laboratory Manual*. Springer Verlag, ISBN: 3540584056, hereby incorporated by reference in its entirety).

Vectors can advantageously contain one or more bacterial or plant-expressible selectable or screenable markers or reporter genes, such that incorporation of the vector into a rice plant cell or protoplast can be monitored. It is preferable that such selectable or screenable markers confer a readily detectable phenotype, such as resistance to an otherwise toxic compound (e.g., kanamycin resistance) or a colorimetric or luminescent reaction upon incubation of the plant with an appropriate substrate (e.g., beta-glucuronidase (GUS) or luciferase genes). Such reporter genes are well known in the art.

The constructs described herein can be introduced to a rice plant or plant cell by any useful method. A large number of processes are available and are well known to deliver genes to plant cells. One of the best-known methods involves the use of *Agrobacterium* or similar soil bacteria as a vector, wherein the *Agrobacterium* is transformed with the construct of interest or a vector containing the construct. Target tissues of a plant are co-cultivated with the transformed *Agrobacterium* which inserts the nucleotide sequence of interest into the plant genome, as is described by U.S. Pat. No. 4,940,838 (Schilperoort et al.; which is incorporated herein by reference in its entirety), and Horsch et al. (1985, *Science* 227:1229-1231; which is incorporated herein by reference). Alternative gene transfer and transformation methods useful in the present invention include, but are not limited to, liposomes, electroporation or chemical-mediated uptake of free DNA, calcium phosphate co-precipitation techniques, targeted microprojectiles and micro- or macroinjection, direct DNA transformation, and may involve Ti plasmids, Ri plasmids, or plant virus vectors. Such transformation methods are well documented in the art. It will be understood by one skilled in the art that the method chosen for rice plant, rice plant cell, or protoplast transformation will in large part be determined by the nature of the OsAnt1 promoter sequence-target sequence construct, or the vector containing the construct.

A transformed *Oryza sativa* plant including a coding region in operative linkage with an OsAnt1 promoter sequence is described. Also provided is *Oryza sativa* plant seed including a coding region in operative linkage with the OsAnt1 promoter sequence described herein. The transformed rice plants and seeds produced according to the present invention may be further useful in breeding programs for the production of rice plants having more than one desired trait. For example, two transformed rice plants of the invention each having expression of a desired transgene may be crossed using known methods to produce progeny that are characterized in having expression of both transgenes. In this manner, it is possible to produce transformed rice plants having a combination of desirable traits expressed in the plant.

Furthermore, it will be understood by one skilled in the art that different varieties of plants may be more or less amenable to genetic manipulation in general; therefore, it may be advantageous to first transform a related varieties of the rice plant by the methods and with the constructs described herein and to subsequently introduce expression of the target gene into the. rice plant by cross-breeding techniques. Such techniques and appropriately related plant varieties are well known to one skilled in the art.

Seeds may be harvested from transformed rice plants using methods well known in the art and further used to re-grow the transformed plants and hybrids described herein.

The methods and constructs described herein allow the production of rice plants and seeds having expression of one or more desired genes in the rice plant. There is a wide variety of possible applications of the plants described herein, including, but not limited to, the production of rice plants having increased stress tolerance, improved nitrogen uptake, improved nitrogen utilization, improved nutrient content, improved nutrient yields of desired compounds, and phytoremediative properties. Specific applications are further described below.

The plants described herein are able to thrive on nutrient-poor soils. It is well known in the art that certain plant species, particularly crop plants, deplete the soil of nutrients necessary to sustain growth, such as nitrogen, phosphate, and potassium. In order to replenish the lacking nutrients, it is necessary either to fertilize the soil (an expensive and environmentally damaging procedure) or to cultivate plants known to deposit the depleted nutrient into the soil (e.g., clover or soybean in the case of nitrogen depletion). However, these alternatives may be less economically acceptable. The methods described herein permit the targeted expression of nucleotide sequences involved in nutrient uptake (for example, transport molecules) to those tissues in which the uptake occurs (for example, the root or root hairs) to thereby improve the ability of the rice plant to absorb the nutrients from the environment.

The methods described herein may also be used to produce rice plants that express heterologous or optimized native nutrient utilization genes or coding regions that permit more efficient use of the nutrient, such that less of the nutrient (for example, nitrogen) is required for the normal growth and functioning of the plant. Further, it is possible, using the methods described herein, to express coding regions of interest involved in the use and uptake of nutrients not normally used by the rice plant suitable in those plant tissues that are directly exposed to the different nutrient (for example, root and leaf). In this manner, rice plants that are able to grow and thrive on different nutrient sources (for example, different nitrogen sources) may be produced. Particularly useful target genes for the optimization of nitrogen efficiency of the plant include: a nitrate transporter (high or low affinity), an ammonium transporter, an ammonia transporter, an amino acid transporter, alanine dehydrogenase, glutamine synthetase (GS), asparagine synthetase (AS), glutamate synthase (also known as glutamate 2:oxogluturate amino transferase and GOGAT), asparaginase (ANS), glutamate dehydrogenase (GDH), nitrate reductase, and an aminotransferase such as alanine aminotransferase (AlaAT) or aspartate aminotransferase (AspAT) such as those described in US Patent Application Publication Number 2005/0044585, which is hereby incorporated by reference in its entirety.

The techniques described herein may be used to produce rice plants that can more efficiently utilize fertilizer input by rapidly taking up the nitrogen provided by the fertilizer and storing it at the time of application, thereby reducing the amounts of nitrogenous fertilizer lost to leaching, etc. This may permit a reduction in the amount of nitrogenous fertilizer required to be applied to a rice crop to obtain crop yields comparable to those obtained using normal cultivation techniques and rice plants that have not been modified according to the present invention. Additional agronomic advantages can include faster growth and rice crop yield, where nitrogenous fertilizer input is maintained at levels used in common crop cultivation techniques.

Transformed *Oryza sativa* plants expressing an oligonucleotide sequence encoding alanine aminotransferase (AlaAT) in operative linkage with the OsAnt1 promoter sequence of the present invention were produced. As shown in Example 3, transformed plants expressing AlaAT under control of the OsAnt1 promoter sequence exhibited higher dry weight biomass and increased seed yields when compared to control plants. These results indicate that rice plants expressing a heterologous AlaAT under the control of OsAnt1 promoter sequence are capable of optimizing the utilization of available nitrogen thereby resulting in an increase in plant biomass, seed yield or a combination thereof.

Therefore, methods for increasing biomass of an *Oryza sativa* plant, including providing an *Oryza sativa* plant with a coding region of interest in operative linkage with an OsAnt1 promoter sequence described herein are described. The coding region of interest may encode an enzyme involved in optimizing nitrogen efficiency of the plant, for example, it may encode alanine aminotransferase (AlaAT) and expression of the coding region suitably takes place in the root.

Also provided is a method for increasing seed yield of an *Oryza sativa* plant, including providing an *Oryza sativa* plant with a coding region in operative linkage with an OsAnt1 promoter sequence described in the present invention. The coding region of interest may encode an enzyme involved in optimizing nitrogen efficiency of the plant, for example, it may encode alanine aminotransferase (AlaAT).

The above description is not intended to limit the claimed invention in any manner; furthermore, the discussed combination of features might not be absolutely necessary for the inventive solution.

The following examples further illustrate certain embodiments of the invention.

EXAMPLES

Example 1

Isolation And Characterization of the OsAnt1 Promoter Sequence

The nucleotide sequence (bp 366-3175) of the btg26 gene (Stroeher et al., 1995, *Plant Mol. Biol.* 27:541-551; accession number S77096) was used to search the nucleotide database at NCBI using the blastn search tool. A rice sequence (accession number AF323586) was identified and this nucleotide sequence was used to search the TIGR *Oryza sativa* sequencing project (tigr.org/tdb/e2k1/osa1/). The rice homologue of btg26, *Oryza sativa* antiquitin (OsAnt1), was identified on chromosome 9 of rice (accession number AP005570; 98524-101189 base pairs). A 973-bp sequence upstream of the start codon of OsAnt1 is shown in FIG. 2 (SEQ ID NO:1). The sequence of the 403 bps upstream (5') of the ATG start codon of the OsAnt1 gene was selected for analysis. To determine if the sequence was likely to function as a promoter sequence, the sequence was analyzed using the TSSP plant promoter prediction software available on the web. The analysis predicted that the sequence was a plant promoter sequence. The most likely location of the TATA box (bold in FIG. 2), as well as other promoter sequence elements, was determined.

Since the projected OsAnt1 promoter sequence was predicted to contain promoter elements according to the prediction software, the sequences were analyzed for promoter motifs that may be recognition sites for transcription factors using Signal Scan Software (Prestridge, 1991; BIMAS website). Five different signal sequences were predicted in the OsAnt1 promoter, including ADR1, DBF-A, GAL4, HSTF and RAF transcription factor binding sites.

The OsAnt1 sequence was compared to nucleic acid sequences of btg26 promoter sequences from *Brassica napus* and *Arabidopsis* using the ClustalW 1.8 multiple sequence alignment software on the BCM Search Launcher homepage (searchlauncher.bcm.tmc.edu/) and BOXSHADE server (ch.embnet.org/software/BOX_form.html). Inspection of conserved nucleotides revealed that the *Brassica* and *Arabidopsis* turgor gene-26 promoter sequences are more similar to each other than to the OsAnt1 sequence. A feature among all three promoter sequences is the polypyrimidine (CT) tracts evident within the nucleotide sequences. These tracts range from 20-22 bases and are found just upstream of the probable TATA boxes in all three promoter sequences. Furthermore, the OsAnt1 sequence has a second polypyrimidine tract just upstream of the ATG start codon.

Rice genomic DNA was isolated from cv. Kitaake. The following PCR primers (positions underlined in FIG. 2) corresponding to the OsAnt1 promoter region were selected:

```
                                        (SEQ ID NO:2)
    Primer 1: AGGAAGTGATTTTTAGCGTAGCTG;

(SEQ ID NO:3)
    Primer 2: ATGGCAGAAGAGAGAGAGAGAGG.
```

Touch-down PCR was conducted using rice genomic DNA and the above primers. A 975-bp fragment was produced. The amplified PCR fragment was ligated into pCR®II-TOPO vector (Invitrogen) and transformed into *E. coli*, TOP 10 cells. The resulting plasmid is designated pT-riceOsAnt1pro.

Sequence analysis indicated that the 975-bp PCR fragment encodes a promoter sequence designated the OsAnt1 promoter sequence. Comparison of the OsAnt1 promoter from cv. Kitaake with that of cv. Nipponbare (obtained from the database) revealed that they share 99.9% identity. The putative TATA box was found 145 bps upstream of the start codon.

Example 2

Genetic Constructs Containing OsAnt1 Promoter Sequence

Genetic constructs containing OsAnt1 promoter sequence driving the beta-glucuronidase (GUS) reporter gene (OsAnt1pro-Gus) or the barley AlaAT gene (OsAnt1pro- AlaAT) were produced using the steps shown schematically in FIGS. 3 and 4, respectively.

RiceOsAnt1pro-GUS Construct

The RiceOsAnt1pro-GUS construct was produced by amplifying the pT-RiceOsAnt1pro template using the following primers:

```
Primer 3: EcoRI-OsAnt1 promoter sequence
                                      (SEQ ID NO:4)
GGAATTCAGGAAGTGATTTTT Primer 4: NcoI-OsAnt1 promoter sequence
                                      (SEQ ID NO:5)
CATGCCATGGATGGCAGAAGA
```

The resultant PCR fragments were ligated into the plant binary vector, pCAMBIA1305.1, digested with EcoR1 and Nco1 to produce a pCAMBIA1305.1-riceOsAnt1pro-GUS construct. The EcoRI and NcoI sequences at the end of primers 3 and 4, respectively, allowed insertion of the PCR fragment into the pCAMBIA1305.1 vector, replacing the existing CaMV35s promoter with the OsAnt1 promoter sequence. The NcoI sequence (CCATGG) includes a Met codon, ATG, which is in frame with the GUS reporter gene and allows expression of the GUS reporter gene from the OsAnt1 promoter sequence.

RiccOsAnt1pro-AlaAT Construct

The RiceOsAnt1pro-AlaAT construct was produced by amplifying the pT-RiceOsAnt1pro template using the following primers:

```
Primer 3: EcoRI-OsAnt1 promoter sequence
                                      (SEQ ID NO:4)
GGAATTCAGGAAGTGATTTTT Primer 5: PstI-OsAnt1 promoter sequence
                                      (SEQ ID NO:5)
AACTGCAGATGGCAGAAGA
``` and the resultant PCR fragments digested with EcoR1 and Pst1 were ligated into the plant binary vector, pCAMBIA1300, digested with EcoR1 and Pst1 to produce pCAMBIA1300-riceOsAnt1pro.

An AlaAT DNA fragment was amplified by PCR using pAG001 as a template. pAG001 is described in U.S. Pat. No. 6,084,153 where it is identified as pbtg26/AlaAT/nos. It contains the btg26 promoter linked to the barley AlaAT gene with a nopaline synthase terminator. The barley AlaAT/nos terminator sequences were amplified from pAG001 using the following primers:

```
Primer 6: PstIAlaAT sequence
                                      (SEQ ID NO:7)
AACTGCAGATGGCTGCCACCG Primer 7: HindIII-NOS terminator sequence
                                      (SEQ ID NO:7)
CCCAAGCTTCCCGATCTAGTA
```

The resulting AlaAT/nos fragment was digested with Pst and HindIII and ligated into the pCAMBIA1300-riceOsAnt1pro digested with Pst1 and HindIII to produce a pCAMBIA1300-riceOsAnt1pro-AlaAT construct.

Example 3

Transformation of Rice Plants With Vectors Including OsAnt1 pCAMBIA1305.1-riceOsAnt1pro-GUS and pCAMBIA1300-riceOsAnt1pro-AlaAT were transferred into *Agrobacterium* strain EHA105 (Hood et al., (1993) *Transgenic Res.* 2: 208-218) by electroporation (Sambrook et al. 1989 in Molecular Cloning, A Laboratory Manual Cold Spring Harbor, N.Y.: Cold Spring Harbor Laboratory Press). *Agrobacterium* cells were plated on solid AB medium (Chilton et al. 1974) containing 50 mg/l kanamycin and incubated at 28° C. for 3 days. The bacteria were then collected with a flat spatula and resuspended in liquid co-cultivation medium (R2-CL, Table 1) by gentle vortexing prior to transforming the rice tissues.

Transformation of Rice

Mature seeds of rice (*Oryza sativa* L. cv. Nipponbare) were used in the transformation experiment. The seeds were dehusked and surface sterilized with 50% bleach plus 0.1% Tween-20 for 10 min followed by dipping (1 min) in 70% (v/v) ethanol and then rinsing five times in sterile distilled water. Following sterilization, seeds were cultured on callus induction medium (NB, Table 1) and incubated for three weeks in the dark at 28° C.

TABLE 1

Medium used for callus induction, inoculation, co-culture, resting phase, selection, regeneration and rooting

| Medium | Composition |
| --- | --- |
| NB[a]<br>Callus induction medium<br>(filter sterilize) | N6 major salt and iron source (Chu (1975) Sci. Sin. 5: 659–668) + B5 major salts and vitamins (Gamborg et al. (1968) Exp. Cell Res. 50: 151–158) + 3AA (100 mg/l L-tryptophan + 500 mg/l L-proline + 500 mg/l L-glutamine) + 500 mg/l casein hydrolysate + 2.0 mg/l 2,4-D + 0.5 mg/l picloram + 30 g/l sucrose, pH 5.8, 0.3% gelrite |
| R2-CL<br>Liquid co-culture medium<br>(filter sterilize) | R2 major and minor salts, vitamins and iron source without sucrose (Ohira et al. (1973) Plant and Cell Physiol. 14:1 113–1121) + 0.25 M glucose + 125 μM acetosyringone + 10 mM MES buffer, pH 5.2 + 50 mM potassium phosphate buffer, pH 5.2 + 400 mg/l L-cysteine + 2.0 mg/l 2,4-D + 0.5 mg/l picloram + 0.5 mg/l BAP, pH 5.2 |

TABLE 1-continued

Medium used for callus induction, inoculation, co-culture,
resting phase, selection, regeneration and rooting

| Medium | Composition |
|---|---|
| R2-CS<br>Solid co-culture medium<br>(filter sterilize) | R2 major and minor salts, vitamins and iron source without sucrose (Ohira et al. (1973) Plant and Cell Physiol. 14:1113–1121) + 0.25 M glucose + 125 µM acetosyringone + 10 mM MES buffer, pH 5.2 + 50 mM potassium phosphate buffer, pH 5.2 + 400 mg/l L-cysteine + 2.0 mg/l 2,4-D + 0.5 mg/l picloram + 0.5 mg/l BAP, pH 5.2 + 0.3% gelrite |
| R2-AS<br>Resting phase<br>(filter sterilize) | R2 major and minor salts, vitamins and iron source without sucrose + 0.25 M sucrose + 0.5 mM acetosyringone + 10 mM MES buffer, pH 5.0 + 50 mM potassium phosphate buffer, pH 5.0 + 10 mM $CaCl_2$ + 400 mg/l L-cysteine + 2.0 mg/l 2,4-D + 0.5 mg/l picloram + 0.5 mg/l BAP + 250 mg/l cefotaxime + 250 mg/l amoxicillin, pH 5.0, 0.3% gelrite |
| R2S<br>Selection medium<br>(filter sterilize) | R2 major and minor salts, vitamins and iron source + 30 g/l sucrose + 2.0 mg/l 2,4-D + 0.5 mg/l picloram + 50 mg/l hygromycin + 250 mg/l cefotaxime + 100 mg/l amoxicillin, pH 5.8, 0.3% gelrite |
| NBS<br>Selection medium-II<br>(filter sterilize) | NB medium + 3AA + 2.0 mg/l 2,4-D + 0.5 mg/l Picloram + 50 mg/l hygromycin + 250 mg/l cefotaxime + 100 mg/l amoxicillin, pH 5.8, 0.3% gelrite |
| PRN<br>Pre-regeneration medium<br>(filter sterilize) | NB medium + 3AA + 5 mg/l ABA + 2 mg/l BAP + 0.5 mg/l NAA + 50 mg/l hygromycin + 100 mg/l cefotaxime + 50 mg/l amoxicillin, pH 5.8, 0.4% gelrite |
| RN<br>Regeneration medium<br>(filter sterilize) | NB medium + 3 mg/l BAP + 0.5 mg/l NAA + 50 mg/l hygromycin + 100 mg/l cefotaxime + 50 mg/l amoxicillin, pH 5.8, 0.4% gelrite |
| R<br>Rooting medium<br>(Autoclave/filter sterilize) | ½MS (Murashige and Skoog (1962) Physiol. Plant 15: 473–497) + 50 mg/l hygromycin + 100 mg/l cefotaxime + 50 mg/l amoxicillin, pH 5.8, 0.3% gelrite |

[a]NB medium with 1.25 mg/l $CuSO_4$
[b]Optional

After three weeks, 3-5 mm long embryogenic nodular units released from the scutellum-derived callus at the explant/medium interface were immersed into 25 ml of liquid co-culture medium (R2-CL, Table 1) containing *Agrobacterium* cells at the density of 3-5×10$^9$ cells/ml ($OD_{600}$=1) in a 100 mm-diameter Petri dish for 10-15 minutes. Embryogenic units were then blotted dry on sterilized filter paper, transferred to a Petri dish containing solid co-culture medium (R2-CS, Table 1) and incubated for three days at 25° C. in the dark. Co-cultured embryogenic calli were then transferred to resting medium (R2-AS, Table 1) and incubated at 28° C. in the dark for a week.

After a week, uncontaminated embryogenic units were then individually transferred to selection medium (R2S, Table 1) containing hygromycin for selection of transformed tissue and incubated at 28° C. in the dark. Following 3 weeks of selection on R2S medium, the embryogenic units that turned dark brown with brownish protuberances arising throughout the callus surface were transferred to NBS selection medium (Table 1). After 5 weeks of co-culture, the protuberances developed into brownish globular structures that were gently teased apart from callus and incubated for 2 weeks in the resealed Petri dish. After 2 weeks, these globular structures converted into round shaped, compact and yellowish calli.

The putatively transgenic, hygromycin-resistant calli were gently picked out, transferred, cultured on pre-regeneration medium (PRN, Table 1) and then incubated for a further week. All of the resistant calli originating from a single co-cultured embryogenic nodular unit were grouped in a sector of the PRN dish. Creamy-white, lobed calli with a smooth and dry appearance were individually transferred to regeneration medium (RN, Table 1), incubated for 2 days in the dark, then maintained for three weeks under a 12/12-h (day/night) photoperiod with light provided at an intensity of 55 µmol/m per sec. Green shoots regenerating from a resistant callus were dissected and sub-cultured in test tube containing rooting medium (R, Table 1) for 1-2 weeks to promote vigorous roots and tillers before being transferred to pots in the growth rooms. Transgenic plants were grown to maturity in 16-cm pots containing soil-less potting mixture (Metromix 220). Plants were maintained in growth rooms set to 28° C. and 14/10 hours day/night photoperiods. Fertilizer was applied twice a week starting two weeks after planting in pots. The fertilizer mix contained 225 g 20/20/20 fertilizer, 50 g of plant micronutrients, 6.1 g of $CuSO_4.5H_2O$, 140 g FeEDTA, 13.8 g $ZnSO_4.7H_2O$, 260 g $MgSO_4.7H_2O$, 3.7 g $H_3BO_3$ for a total of 712.4 g. Two grams of the fertilizer mix are dissolved in 8 liters of water and applied twice a week to 24 plants.

Analysis of Expression Directed By the OsAnt1 Promoter Sequence

Induction of expression directed by the OsAnt1 promoter sequence was examined using rice plants transformed with the OsAnt1pro-GUS construct. Plants were germinated and grown hydroponically in sterile conditions in Magenta jars. Two-week-old plants were stained for in vivo GUS activity by injecting into the root media 5 mls of 50 mM phosphate buffer (pH 7.5) containing 0.2 mM X-gluc (5-bromo-4-chloro-3-indolyl-beta-glucuronic acid) and incubating the plants in this media for 1-24 hours. Root tissue was then viewed under a dissection microscope and photographs were taken, which are shown in FIG. 5.

Dark stained areas in FIG. 5 indicate expression of the GUS reporter gene. There is no expression of the GUS reporter gene driven by the OsAnt1 promoter in the root tip (specifically the dividing cells); however, expression begins very quickly in the cell expansion zone, just behind the root tip. The OsAnt1 promoter sequence directed expression of the GUS reporter gene in the root hairs as well. Further from the root tip in more mature roots, expression is lost from the main root, but lateral roots stain very heavily, indicating that OsAnt1 directs expression in these lateral roots very strongly.

Analysis of Transformed Plants Containing the AlaAT Construct

Fifty-eight OsAnt1/AlaAT/NOS transgenic plants were generated and measurements for flowering, tiller number, seed weights and biomass at maturity were recorded for the $T_0$ generation plants.

The dry weight biomass of OsAnt1/AlaAT plants and control plants was measured at maturity, and the data is presented in FIG. 6. The average biomass of the transgenic OsAnt1/AlaAT plants was higher than the average biomass of control plants.

Seeds were collected from OsAnt1/AlaAT plants and control plants at maturity and the total weight of the seeds was measured. The results are shown in FIG. 7, which shows that the total seed weight of seeds collected from OsAnt1/AlaAT plants was higher than that of the seed weight from control plants.

FIG. 8 shows the relationship between dry weight biomass and total seed weight for each transgenic plant. A substantially linear correlation is shown, which indicates that an increase in biomass results in a corresponding increase in total seed weight in OsAnt1/AlaAT plants.

These results indicate that OsAnt1/AlaAT transgenic plants are capable of optimizing the utilization of available nutrients thereby resulting in an increase in plant biomass, seed yield or a combination thereof.

All citations listed herein are hereby incorporated by reference in their entirety.

The present invention has been described with regard to one or more embodiments. However, it will be apparent to persons skilled in the art that a number of variations and modifications can be made without departing from the scope of the invention as defined in the claims.

What is claimed is:

1. An isolated *Oryza sativa* antiquitin (OsAnt1) promoter sequence consisting of SEQ ID NO: 1.

2. A genetic construct comprising the OsAnt1 promoter sequence of claim 1 operatively linked with a target protein coding sequence.

3. The genetic construct of claim 2, wherein the target protein is a nitrogen utilization protein.

4. The genetic construct of claim 3, wherein the nitrogen utilization protein is selected from the group consisting of: a high affinity nitrate transporter, a low affinity nitrate transporter, an ammonium transporter, an ammonia transporter, an amino acid transporter, alanine dehydrogenase, glutamine synthetase, asparagine synthetase, glutamate synthase, glutamate 2:oxogluturate amino transferase, asparaginase, glutamate dehydrogenase, nitrate reductase, aspartate aminotransferase, and alanine aminotransferase.

5. The genetic construct of claim 4, wherein the nitrogen utilization protein is alanine aminotransferase.

6. A vector including the genetic construct of claim 2.

7. A transformed *Oryza sativa* plant comprising a target gene in operative linkage with a recombinant OsAnt1 promoter sequence consisting of SEQ ID NO: 1.

8. The method of claim 7, wherein the target gene encodes a nitrogen utilization protein selected from the group consisting of a high affinity nitrate transporter, a low affinity nitrate transporter, an ammonium transporter, an ammonia transporter, an amino acid transporter, alanine dehydrogenase, glutamine synthetase, asparagine synthetase, glutamate synthase, glutamate 2:oxogluturate amino transferase, asparaginase, glutamate dehydrogenase, nitrate reductase, aspartate aminotransferase and alanine aminotransferase.

9. The method of claim 8, wherein the nitrogen utilization protein is alanine aminotransferase.

10. An *Oryza sativa* plant seed comprising a target gene in operative linkage with a recombinant OsAnt1 promoter sequence consisting of SEQ ID NO: 1.

11. The seed of claim 10, wherein the target gene encodes a nitrogen utilization protein selected from the group consisting of a high affinity nitrate transporter, a low affinity nitrate transporter, an ammonium transporter, an ammonia transporter, an amino acid transporter, alanine dehydrogenase, glutamine synthetase, asparagine synthetase, glutamate synthase, glutamate 2:oxogluturate amino transferase, asparaginase, glutamate dehydrogenase, nitrate reductase, aspartate aminotransferase and alanine aminotransferase.

12. The seed of claim 11, wherein the nitrogen utilization protein is alanine aminotransferase.

* * * * *

UNITED STATES PATENT AND TRADEMARK OFFICE
CERTIFICATE OF CORRECTION

| | |
|---|---|
| PATENT NO. | : 7,560,626 B2 |
| APPLICATION NO. | : 11/644453 |
| DATED | : July 14, 2009 |
| INVENTOR(S) | : Allen G. Good et al. |

It is certified that error appears in the above-identified patent and that said Letters Patent is hereby corrected as shown below:

In column 19, line 24, in claim 8, delete "method" and insert -- plant --.

In column 20, line 8, in claim 9, delete "method" and insert -- plant --.

Signed and Sealed this
First Day of February, 2011

David J. Kappos
*Director of the United States Patent and Trademark Office*